(12) United States Patent
Hsiao

(10) Patent No.: US 11,524,089 B2
(45) Date of Patent: Dec. 13, 2022

(54) HAND WASH CLEANING AND ENVIRONMENTAL PURIFICATION DIFFUSER

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 77 days.

(21) Appl. No.: 17/125,055

(22) Filed: Dec. 17, 2020

(65) Prior Publication Data

US 2021/0106713 A1 Apr. 15, 2021

Related U.S. Application Data

(63) Continuation-in-part of application No. 16/259,833, filed on Jan. 28, 2019, now Pat. No. 11,154,633, and a continuation-in-part of application No. 17/102,236, filed on Nov. 23, 2020, and a continuation-in-part of application No. 17/247,252, filed on Dec. 4, 2020, said application No. 16/259,833 is a continuation-in-part of application No. 16/157,994, filed on Oct. 11, 2018, now Pat. No. 11,045,570, said application No. 17/102,236 is a continuation-in-part of application No. 16/259,833, filed on Jan. 28, 2019, now Pat. No. 11,154,633, and a continuation-in-part of application No. 16/157,994, filed on Oct. 11, 2018, (Continued)

(51) Int. Cl.
*A61L 9/12* (2006.01)
*A47K 7/00* (2006.01)

(52) U.S. Cl.
CPC ............... *A61L 9/122* (2013.01); *A47K 7/00* (2013.01); *A61L 2209/12* (2013.01); *A61L 2209/13* (2013.01)

(58) Field of Classification Search
CPC ........ A61L 9/14; A61L 9/122; A61L 2209/13; B05B 7/0012; B05B 17/0615
See application file for complete search history.

(56) References Cited

U.S. PATENT DOCUMENTS 7,963,460 B2 * 6/2011 Jorgensen ............... A61L 9/122
239/289
7,992,801 B2 8/2011 Hsiao
(Continued)

*Primary Examiner* — Thien S Tran
(74) *Attorney, Agent, or Firm* — Sinorica LLC

(57) ABSTRACT

A hand wash cleaning and environmental purification diffuser includes tank cover covered on a slot of a water tank in a bottom shell, a diffusing cover assembled to an opening of the bottom shell to shield the tank cover, an air flow channel formed in the oscillation space in the water tank and shaped like a tubular bulge so that when the diffuser is dumped, the liquid in the water tank is less likely to seep directly into the interior of the diffuser or the environment, two oscillators mounted in the oscillation space in the water tank and respectively coated with a layer of acid and alkali resistant coating, users can add safe cleaning liquids such as alkaline ionized water to the oscillation space and atomize into a cleaning mist, which can be used as deodorization and sterilization for hand cleaning, disinfection and environmental purification, and is safe to use.

17 Claims, 5 Drawing Sheets

Related U.S. Application Data now Pat. No. 11,045,570, said application No. 17/247,252 is a continuation-in-part of application No. 17/102,236, filed on Nov. 23, 2020, and a continuation-in-part of application No. 16/259,833, filed on Jan. 28, 2019, now Pat. No. 11,154,633, and a continuation-in-part of application No. 16/157,994, filed on Oct. 11, 2018, now Pat. No. 11,045,570.

(56) References Cited

U.S. PATENT DOCUMENTS

| | | | |
|---|---|---|---|
| 8,029,153 B2 * | 10/2011 | Jorgensen | A61L 9/14 362/253 |
| 8,133,440 B2 * | 3/2012 | Jorgensen | A61L 9/14 422/123 |
| 8,196,903 B2 * | 6/2012 | Jorgensen | A61L 9/14 261/78.2 |
| 8,569,050 B1 * | 10/2013 | Ericsson | C12M 21/02 435/292.1 |
| 8,983,277 B2 | 3/2015 | Hsiao | |
| 9,206,963 B2 | 12/2015 | Hsiao | |
| 9,410,695 B2 | 8/2016 | Hsiao | |
| 9,498,553 B2 | 11/2016 | Hsiao et al. | |
| 9,500,358 B2 | 11/2016 | Hsiao | |
| 9,844,609 B2 | 12/2017 | Hsiao | |
| 10,064,969 B2 | 9/2018 | Hsiao | |
| 2010/0308129 A1 * | 12/2010 | Jorgensen | A61L 9/14 239/34 |
| 2011/0024521 A1 * | 2/2011 | Jorgensen | A61L 9/14 239/289 |
| 2011/0049266 A1 * | 3/2011 | Jorgensen | A61L 9/12 239/338 |
| 2011/0051983 A1 * | 3/2011 | Jorgensen | A61L 9/122 381/386 |
| 2011/0079660 A1 * | 4/2011 | Jorgensen | B05B 17/0615 239/289 |
| 2011/0080724 A1 * | 4/2011 | Jorgensen | A61L 9/14 239/338 |
| 2012/0251296 A1 * | 10/2012 | Jorgensen | B05B 17/0607 415/116 |
| 2014/0263722 A1 * | 9/2014 | Hsiao | A61L 9/122 239/102.2 |
| 2014/0263723 A1 * | 9/2014 | Hsiao | B05B 7/0012 239/102.2 |
| 2015/0109823 A1 * | 4/2015 | Hsiao | A61L 9/02 362/643 |
| 2015/0117056 A1 * | 4/2015 | Hsiao | A61L 9/03 362/611 |
| 2016/0175755 A1 * | 6/2016 | Nakamura | B01D 46/429 55/385.6 |
| 2016/0192801 A1 * | 7/2016 | Wu | A47J 27/10 99/330 |
| 2016/0195257 A1 * | 7/2016 | Hsiao | F21V 33/0004 362/92 |
| 2021/0086220 A1 * | 3/2021 | Hasik | B05B 17/0646 |
| 2022/0072183 A1 * | 3/2022 | Zou | A61L 9/14 |

* cited by examiner

HAND WASH CLEANING AND ENVIRONMENTAL PURIFICATION DIFFUSER

The present invention is a continuation-in-part of patent application Ser. No. 16/259,833 filed on Jan. 28, 2019 and Ser. No. 17/102,236 filed on Nov. 23, 2020 and patent application Ser. No. 17/247,252 filed on Dec. 4, 2020.

BACKGROUND OF THE INVENTION

1. Field of the Invention

The present invention relates to scent releasing devices and more specifically, to a hand wash cleaning and environmental purification diffuser.

2. Description of the Related Art

The existing environment cleaning, deodorization, sterilization, disinfection and other operations usually use bleach, alcohol, and other solutions, which can cause irritation, corrosion and residue, or other allergies or discomfort to the human body. Alcohol spraying devices often leave alcohol drips on the table. This safety issue should not be careless.

These liquid alcohol or bleach are not suitable for spraying in the space. Therefore, the scope of cleaning is difficult to take into account the three-dimensional space or the indoor furnishings above the ground. Some gaseous fragrance or insecticide spray devices use electrical components. When the spray device filled with corrosive liquid inside is dumped, the corrosive liquid overflowing the spray device is also easy to cause environmental pollution and harm to the human body, and it is not safe to use. In addition, the water tank of the spray device contains corrosive acid liquid that easily corrodes the oscillator, causing damage to the electrode layer and the problem that the formation of spray cannot produce a better environmental effect.

SUMMARY OF THE INVENTION

The present invention has been accomplished under the circumstances in view. It is therefore an object of the present invention to provide a hand wash cleaning and environmental purification diffuser, that can use alkaline ionized water liquid, The alkaline ionized water mist produced is non-toxic, non-irritating, and non-residual, and the user's hands can be placed above the diffuser, and the atomized gaseous cleaning liquid can be diffused to clean and disinfect the user's hands. The diffused mist cleans, sterilizes, deodorizes and disinfects the environment to purity the environmental space, which is safe for the environment and does not harm human health.

It is another object of the present invention to provide hand wash cleaning and environmental purification diffuser that includes decoration and lighting combined with diffusing effects to create a better atmosphere for the environment.

To achieve these and other objects of the present invention, a hand wash cleaning and environmental purification diffuser comprises a bottom shell, a first fan, a water tank, a first oscillation device, a diffusing cover and a control unit. The bottom shell comprises a chamber internally defined, a first air inlet provided on a bottom side of the chamber, and an opening formed on an upper edge of the chamber. The water tank is combined in the chamber, comprising a slot, an oscillation space, a tank bottom, a first hole, a tank cover and an air flow channel. The slot is formed on an upper side of the water tank. The interior of the water tank defines the oscillation space containing a liquid. The tank bottom opens the first hole. The air flow channel has one side thereof protruding in the oscillation space of the water tank to form a protruding pipe vent, and an opposite side thereof extending out of the tank bottom to form a vent. The air flow channel is disposed in communication with the first air inlet through the chamber. The first fan is combined in the vent and disposed in communication with the first air inlet through the chamber. The tank cover comprises a shield and a first exhaust hole. The shield forms a recess shape on an inner side of the circumference of the tank cover. The first exhaust hole is formed on an opposite side of the tank cover. The tank cover is detachably covered on the slot. The shield covers the outside of the protruding pipe vent. The protruding pipe vent and the first exhaust hole are disposed in communication with the oscillation space. The first oscillation device is mounted in the first hole and comprises a first oscillator. The first oscillator is externally coated with a layer of acid and alkali resistant coating. The diffusing cover comprises a diffusing hole. The diffusing cover is detachably assembled in the opening of the bottom shell to shield the tank cover. The diffusing hole communicates with the first exhaust hole and the oscillation space. The control unit is combined in the chamber at one side of the tank bottom and electrically connected with the first oscillation device and the first fan.

In this way, connect a power supply to the control unit and instruct the first oscillation device to oscillate the liquid in the oscillation space (such as alkaline ionized water or various environmental cleaning and purification agents) to generate atomized mist, which is output to the external environment as a house furnishing including three-dimensional space or above the ground to sterilize, clean, deodorize, eliminate viruses or purify the air, and the safety of use does not affect human health.

Preferably, the diffuser further comprises a second oscillation device and a sensor. The water tank further comprises a second hole formed on the tank bottom. The second oscillation device is combined with the second hole to cooperate with the first oscillation device to vibrate and atomize the liquid in the oscillation space to greatly increase the molecular weight of the atomized water.

The acid and alkali resistant coating comprises a fluorine-containing polymer (fluoropolymer) or fluorine-containing oligomers or electronic metal coating agent.

The control unit is electrically connected with the sensor. Thereby, the user's hand is placed above the diffusing cover of the diffuser of the present invention, the sensor detects the hand signal, and transmits the hand signal to the control unit. At this time, the control unit instructs the second oscillation device to operate, and cooperate with the first oscillation device to oscillate the alkaline ionized water (in the embodiment, the pH value of the hydroxide ionized water electrolyzed with pure water is about 10 to 12.5) in the oscillation space, thereby generating a larger amount of atomized mist (fine water molecules), so that the water mist and water molecules can be output to the user's hands for hand cleaning, sterilization, and disinfection. It is safe to use, and the hydroxide ion water will not corrode and damage the hands, which improves the injury problem of the usual alcohol or chemical cleaning liquid.

DETAILED DESCRIPTION OF THE PREFERRED EMBODIMENT

Figure 1:
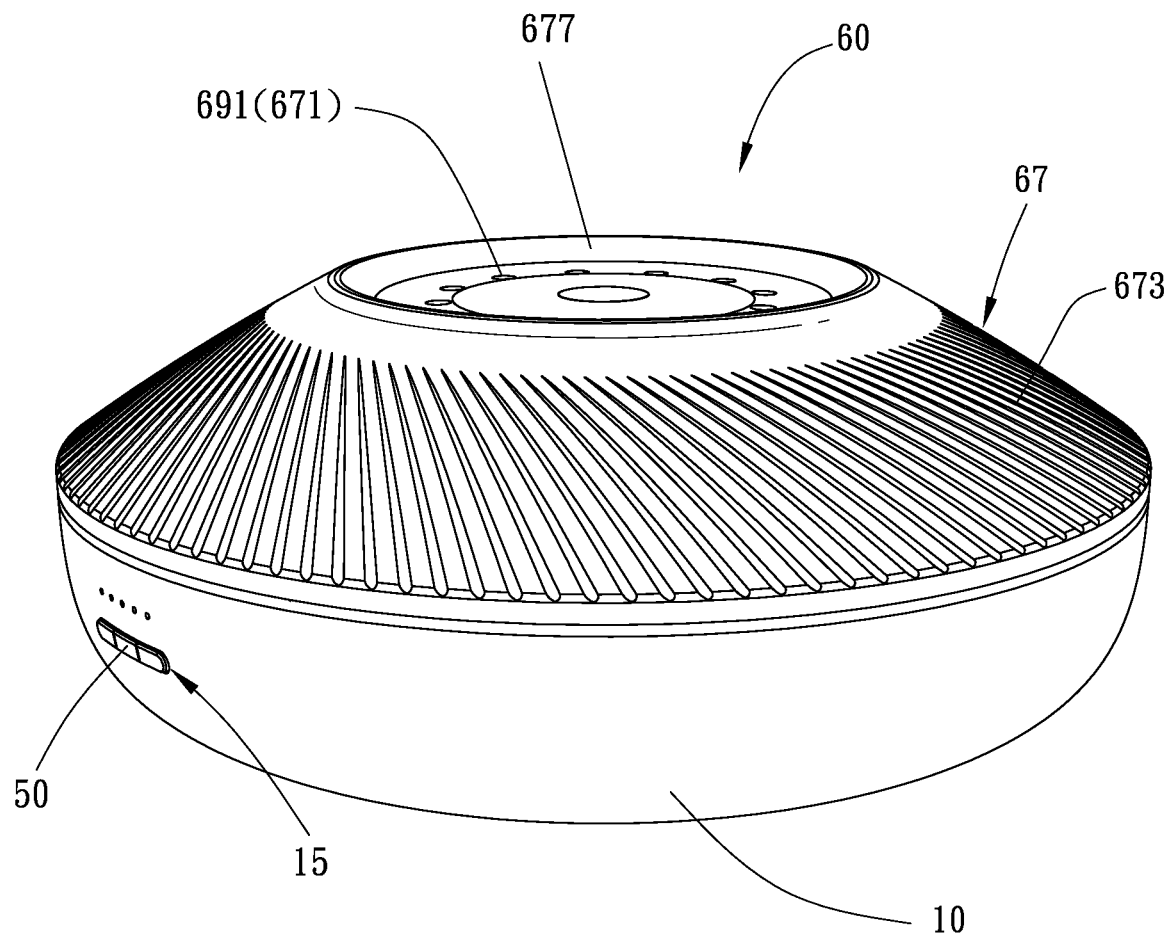
FIG. 1 is an oblique top elevational view of a hand wash cleaning and environmental purification diffuser in accordance with the present invention.

Referring to FIGS. 1-5, a hand wash cleaning and environmental purification diffuser in accordance with the present invention is shown. The hand wash cleaning and environmental purification diffuser comprises a bottom shell 10, a first fan 20, a water tank 30, a first oscillation device 40, a diffusing cover 60, and a control unit 70.

The bottom shell 10 comprises a chamber 11 internally defined, a first air inlet 12 provided on the bottom side of the chamber 11, and an opening 13 formed on the upper edge of the chamber 11.

The water tank 30 comprises a slot 31, an oscillation space 32, a tank bottom 33, a first hole 34, a tank cover 35, and an air flow channel 37. The slot 31 is formed on the upper side of the water tank 30. The interior of the water tank 30 defines the oscillation space 32 containing a liquid. The tank bottom 33 opens the first hole 34. One side of the air flow channel 37 protrudes in the oscillation space 32 of the water tank 30 to form a protruding pipe vent 371, and the other side of the air flow channel 37 extends out of the tank bottom 33 to form a vent 373. The first fan 20 is combined in the vent 373.

The water tank 30 is combined in the chamber 11. The air flow channel 37 and the first fan 20 are disposed in communication with the first air inlet 12 through the chamber 11. The first air inlet 12 provides a path for the first fan 20 to inhale outside air.

The tank cover 35 comprises a shield 355 and a first exhaust hole 357. The tank cover 35 is shaped to match the structure of the protruding pipe vent 371 in the water tank 30. The shield 355 forms a recess shape on the inner side of the circumference of the tank cover 35. The inner side of the recess shape of the shield 355 forms a shielded space. The first exhaust hole 357 is formed on the other side of the tank cover 35. The tank cover 35 is detachably covered on the slot 31, while the shield 355 covers the outside of the protruding pipe vent 371. The protruding pipe vent 371 and the first exhaust hole 357 are disposed in communication with the oscillation space 32.

The first oscillation device 40 is mounted in the first hole 34, comprising a first oscillator 43. The first oscillator 43 is externally coated with a layer of acid and alkali resistant coating for vibrating and atomizing the liquid in the oscillation space 32.

The diffusing cover 60 comprises a diffusing hole 671. The diffusing cover 60 is detachably assembled in the opening 13 of the bottom shell 10 to shield the tank cover 35. The diffusing hole 671 communicates with the first exhaust hole 357 and the oscillation space 32 to form a diffusing outlet path.

The control unit 70 is combined in the chamber 11 at one side of the tank bottom 33, comprising a circuit device, such as PCBA, and a driver circuit for driving the first oscillation device 40 and the first fan 20. The control unit 70 is electrically connected with the first oscillation device 40, the first fan 20, or other lamps, electronics or appliances used in the diffuser, to control the switching or various action functions of the first oscillation device 40 or the first fan 20 or other lamps, electronics or appliances.

When a power source is connected to the control unit 70, the control unit 70 turns on the first oscillation device 40 to oscillate the liquid in the oscillation space 32 (such as alkaline ionized water or various environmental cleaning and purification preparations, or adding various natural sterilization and deodorants to the applied liquid, thereby producing atomized mist (fine water molecules). At the same time, the fan 20 continues sending the air flow from the first air inlet 12 to the vent 373 to pass through the protruding pipe vent 371 of the air flow channel 37. The airflow is blocked by the shield 355 and flows in the oscillation space 32, and will not directly flow out of the first exhaust hole 357. It can effectively transport the mist (fine water molecules) of the vaporized alkaline ionized water (in the embodiment, the pH value of the hydroxide ionized water electrolyzed with pure water is about 10 to 12.5) from the oscillation space 32 through the first exhaust hole 357 and the diffusing hole 671 to the external environment space to sterilize, clean, deodorize, eliminate viruses or purify the air in a three-dimensional space in a house or above the ground. It is safe to use does not affect human health.

Referring to FIGS. 1-5, the diffuser further comprises a second oscillation device 45 and a sensor 90. Said control unit is electrically connected with said second oscillation device and the sensor 90.

The water tank 30 further comprises a second hole 36. The tank bottom 33 opens the second hole 36 at the bottom side of the oscillation space 32. The second oscillation device 45 is combined in the second hole 36, comprising a second oscillator 48. The second oscillator 48 is externally coated with a layer of acid and alkali resistant coating, and is used in conjunction with the first oscillator 40 to oscillate and atomize the liquid in the oscillation space 32 to greatly increase the molecular weight of the atomized water.

The sensor 90 is combined in the chamber 11 at one side of the tank bottom 33. The control unit 70 is electrically connected to the sensor 90 to power on/off the sensor 90 and receive the detection signal of the sensor 90, and transmit it to the second oscillation device 45 to turn on or turn off.

The sensor 90 can be, for example, a microwave sensor, an infrared sensor or a laser sensor, etc., in the embodiment, a microwave sensor is used, and the microwave penetrates the diffuser to sense whether the user's hand is above the diffuser.

In a preferred embodiment, multiple diffusing holes 671 are provided and distributed on the diffusing cover 67. With this, the atomized mist can be output from the multiple diffusing holes 671.

Thereby, the user's hand is placed above the diffusing cover 60 of the diffuser of the present invention, the sensor 90 detects the hand signal, and transmits the hand signal to the control unit 70. At this time, the control unit 70 instructs the second oscillation device 45 to operate, and cooperate with the first oscillation device 40 to oscillate the alkaline ionized water (in the embodiment, the pH value of the hydroxide ionized water electrolyzed with pure water is about 10 to 12.5) in the oscillation space 32, thereby generating a larger amount of atomized mist (fine water molecules) than the previous embodiment. At the same time, the first fan 20 continues to deliver air flow from the first air inlet 12 to the vent 373, passing through the protruding pipe vent 371 of the air flow channel 37. The airflow is blocked by the shield 355 and flows in the oscillation space 32, which can transport a relatively large amount of highly alkaline electrolyzed hydroxide ion water mist and water molecules through the first exhaust hole 357, so that the water mist and water molecules can be diffused out of the diffusing hole 671 and uniformly dispersed and output to the user's hands for hand cleaning, sterilization, and disinfection. It is safe to use, and the hydroxide ion water will not corrode and damage the hands, which improves the injury problem of the usual alcohol or chemical cleaning liquid.

Referring to FIGS. 2-5, in some embodiments, the diameter of the vent 373 is larger than the protruding pipe vent 371, so that the air flow of the first fan 20 flows from the vent 373 to the protruding pipe vent 371, and the pressure air with a higher flow rate can flow to the oscillation space 32. Thus, the generated mist can be quickly and effectively transported by the air flow to the diffusing hole 671 to escape to the outside of the diffuser. These large increase in atomized gas water molecules will not stay in the atomization space and fall into the liquid, and at the same time, the user's hands are placed above the diffusing cover 60 of the diffuser of the present invention. At the moment of use, the user's hands can immediately receive the cleaning and sterilization effects of a rapid large number of mist, and it is quick and convenient to use without a sense of waiting.

Figure 2:
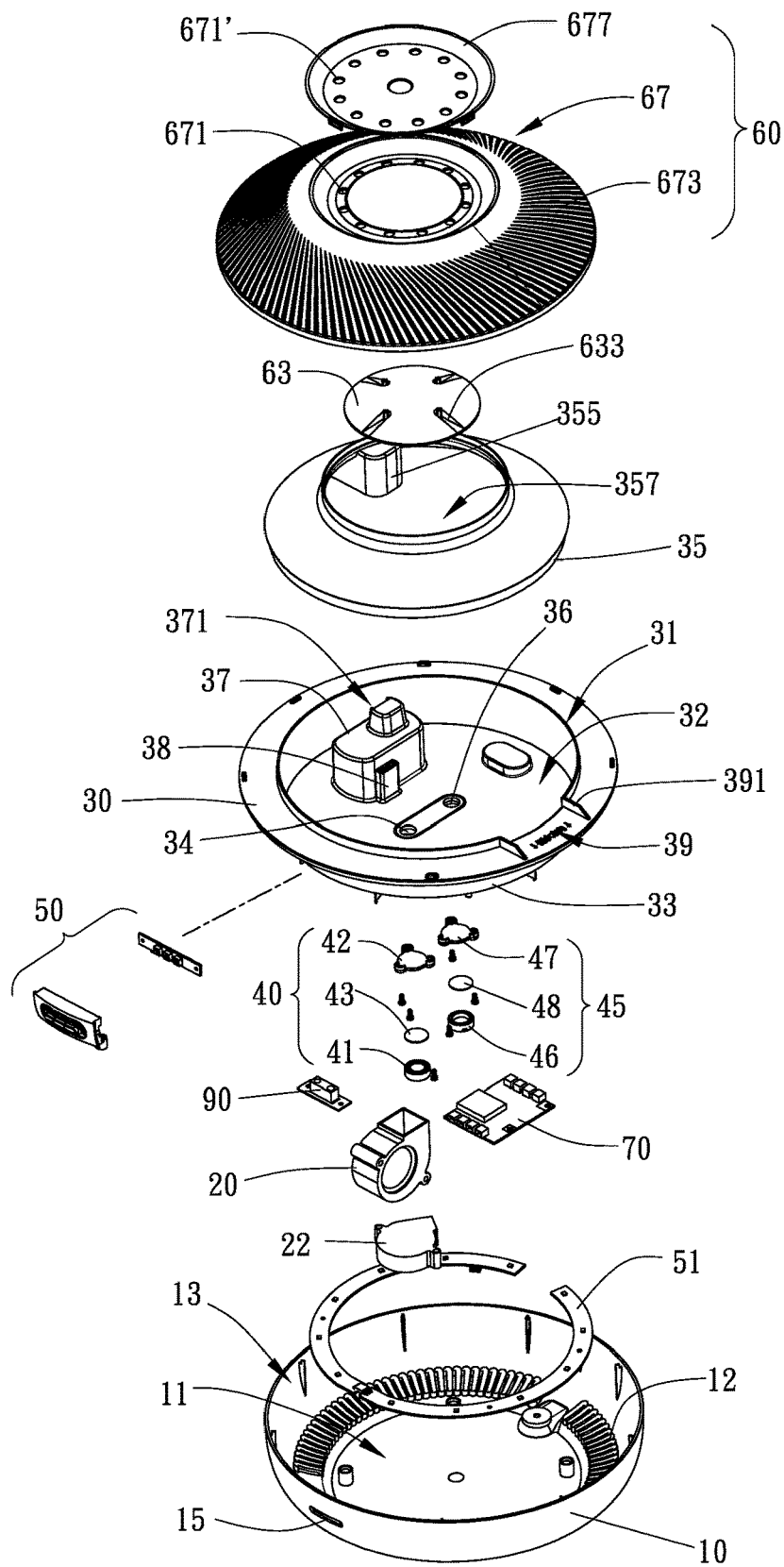
FIG. 2 is an exploded view of the hand wash cleaning and environmental purification diffuser in accordance with the present invention.
Figure 3:
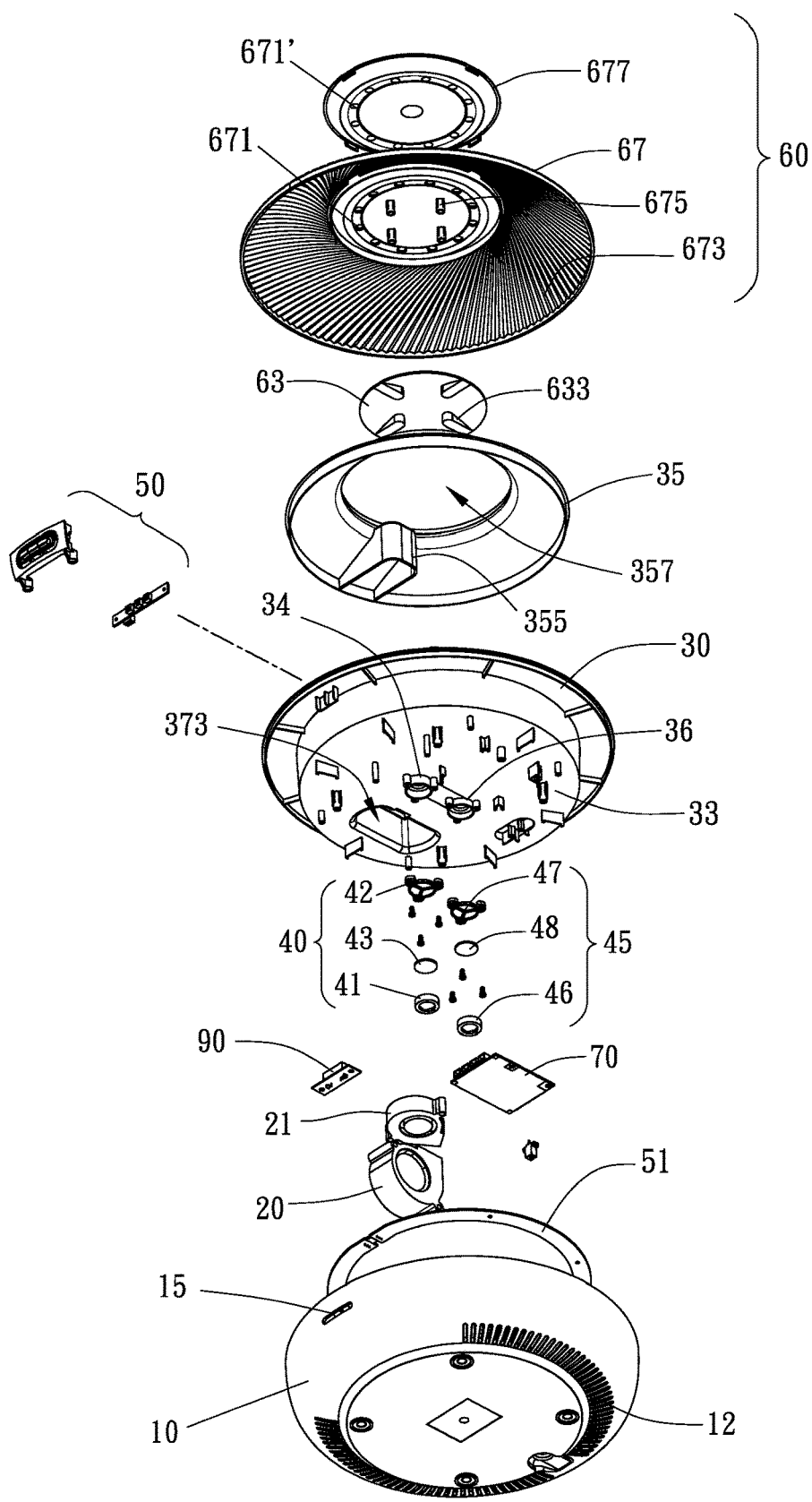
FIG. 3 corresponds to FIG. 2 when viewed from another angle.
Figure 4:
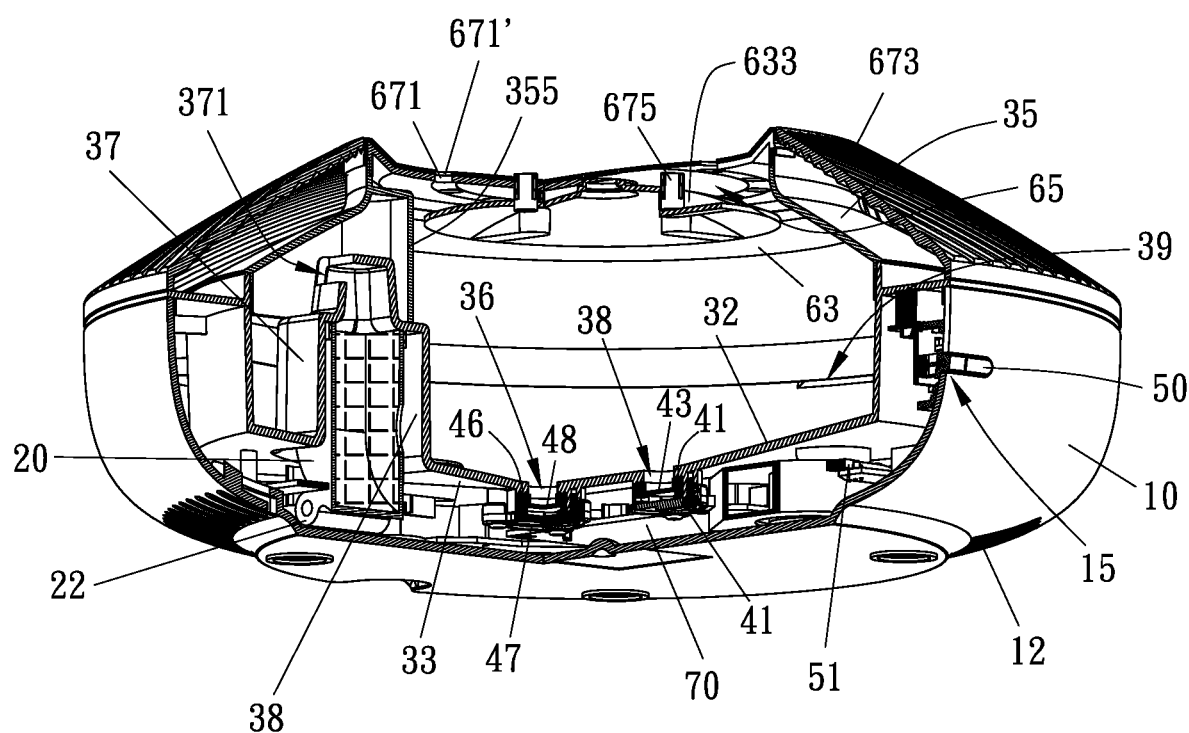
FIG. 4 is a sectional view of a part of FIG. 1.
Figure 5:
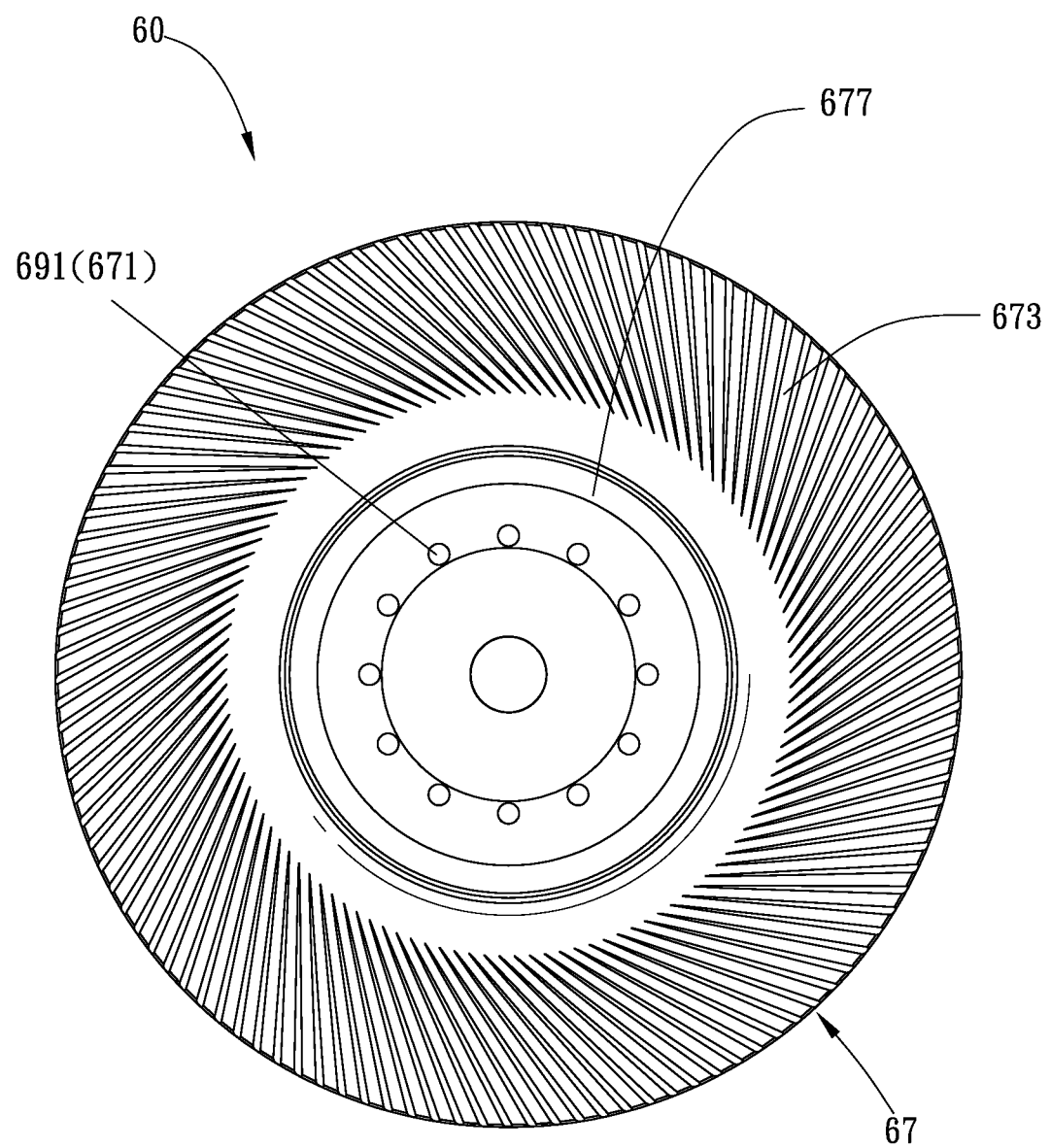
FIG. 5 is a top view of FIG. 1.

Referring to FIGS. 2-4, in one embodiment of the present invention, the first oscillation device 40 comprises a first waterproof ring 41, a first fixing frame 42, and a first oscillator 43. The second oscillation device 45 comprises a second waterproof ring 46, a second fixing frame 47, and a second oscillator 48. The first oscillator 43 and the second oscillator 48 can be, for example, a ceramic sheet or metal sheet material, such as iron or copper, and the outer layer of the first oscillator 43 and the outer layer of the second oscillator 48 are respectively coated with an acid and alkali resistant coating to avoid, for example, alkaline ionized water or various environmental cleaning purification agents, or deodorant, disinfectant liquid from corroding the first oscillator 43 or second oscillator 48 and causing damage. In one embodiment, the film thickness of the acid and alkali resistant coating is 0.5 to 1.5 microns, or preferably about 1 micron. The acid and alkali resistant coating wherein said acid and alkali resistant coating comprises a fluorine-containing polymer (fluoropolymer) or fluorine-containing oligomers or electronic metal coating agent or electronic metal coating agents commonly used in the electronics industry. The first oscillation device 40 is set in the first hole 34 at the bottom side of the oscillation space 351. The first oscillator 43 is set in the first waterproof ring 41, and then the first waterproof ring 41 is mounted in the first hole 34. The first fixing frame 42 is located at the bottom side of the first waterproof ring 41 and fastened to the bottom surface of the tank bottom 33 around the first hole 34 to fix the first oscillation device 40 in position. The second oscillation device 45 is set in the second hole 36. The second oscillator 48 is set in the second waterproof ring 46, and then the second waterproof ring 46 is mounted in the second hole 36. The second fixing frame 47 is located at the bottom side of the second waterproof ring 46 and fastened to the bottom surface of the tank bottom 33 around the second hole 34 to fix the second oscillation device 45 in position. The first oscillator 43 and the second oscillator 48 are protected by the respective acid and alkali resistant coatings. The diffuser of the present invention can use alkaline ionized water electrolyzed by natural pure water (for example, the pH value of hydroxide ionized water electrolyzed by pure water is about 10 to 12.5) to clean, sterilize, deodorize, and disinfect the environment to purify the environmental space.

The first waterproof ring 41 or second waterproof ring 46 can be made of silicon rubber, rubber or plastics.

Referring to FIGS. 1-4, in one embodiment of the present invention, the tank cover 35 covers the first slot 31. The shield 355 covers the outside of the protruding pipe vent 371 of the air flow channel 37. The protruding pipe vent 371 forms a height (distance) relative to the inner wall of the tank cover 35. Thereby, the protruding pipe vent 371, which is designed with a tubular protrusion in the water tank 30, has a height (distance) formed relative to the inner wall of the water tank 30. When the hand wash cleaning and environmental purification diffuser is dumped, the liquid in the water tank 30 can avoid the part of the protruding pipe vent 371 under the influence of gravity, and can be poured on the inner wall of the water tank 30. Therefore, the inclined liquid is less likely to flow directly into the protruding pipe vent 3711, and the liquid is not easy to enter the inside of the hand wash cleaning and environmental purification diffuser, which helps to avoid damage to the electronic parts and electrical contacts of the control unit 70 and the first fan 20. When replenishing liquids such as alkaline ionized water or various environmental cleaning and purifying agents in the oscillation space 32, the diffusing cover 60 can easily be opened from the slot 31 of the water tank 30, and the tank cover 35 can also easily be detached from the slot 37. The user can arbitrarily open the diffusing cover 60 and tank cover 35 from the water tank 30 and cover the diffusing cover 60 and tank cover 35 to the water tank 30 to replenish the liquid, and the structure is simple and convenient to use.

Referring to FIGS. 2-4, in one embodiment of the present invention, the vent opening direction of the protruding pipe vent 371 is perpendicular to the inner side wall of the tank cover 35 and at the same time facing the inner side wall of the tank cover 35 (the protruding tube vent 371 is a horizontal opening). Thereby, when the hand wash cleaning and environmental purification diffuser is dumped, the liquid gravity flow direction (downward) in the water tank 30 that leans into the vent opening direction of the protruding pipe vent 371 is opposite to the vent opening direction of the protruding pipe vent 371. The liquid is not easy to flow upwards into the protruding pipe vent 371 under the influence of gravity, and the liquid in the water tank 30 is more difficult to enter the interior of the hand wash cleaning and environmental purification diffuser.

Referring to FIGS. 2-5, in one embodiment of the present invention, the diffusing cover 60 further comprises an umbrella-shaped panel 67. The umbrella-shaped panel 67 is opened with the diffusing hole 671. The umbrella-shaped panel 67 thinks about the skeleton structure and visual appearance aesthetics of paper umbrellas from Hakka culture. The umbrella-shaped panel 67 comprises a plurality of radial ribs 673. These radial ribs 673 radiate from the outer edge of the spray hole 671 of the umbrella-shaped panel 67 to the peripheral edge of the umbrella-shaped panel 67. These radial ribs 673, like the ribs of a paper umbrella, have support and decoration functions, which promote the umbrella-shaped panel 67 to have higher rigidity. At the same time, the production of the umbrella-shaped panel 67 can also reduce the material and weight. According to this design, the umbrella-shaped panel 67 can be thinner and lighter in weight. It is decorative and not easy to damage during assembly or when dumping.

In some embodiments of the present invention, the radial ribs 673 are arranged on the inner surface of the umbrella-shaped panel 67 and radially extended from the spray hole 671 to the peripheral edge of the umbrella-shaped panel 67. The material of the umbrella-shaped panel 67 can be selected from a variety of light-permeable translucent or transparent plastic materials, acrylic, glass, etc. The light-permeable translucent or translucent or transparent umbrella-shaped panel 67 vaguely sees through the radial ribs 673. The overall shape is like a paper umbrella, with a decorative effect.

Referring to FIGS. 2-4, in one embodiment of the present invention, the diffusing cover 60 further comprises a water baffle 63. The water baffle 63 is combined with the lower side of the umbrella-shaped panel 67. A gap 65 is maintained between the water baffle 63 and the umbrella-shaped panel 67.

The replenished liquid such as alkaline ionized water is oscillated into a mist in the oscillation space 32, and the mist flows from the first exhaust hole 357 through the third gap 354, and then outputs from the diffusing hole 671 of the diffusing cover 60 to the external space. The oscillating liquid in the oscillation space 351 may not be completely atomized by the oscillators 40, 45, and the larger water droplets produced are diffused upward, and the water baffle 63 blocks the water droplets to prevent the water droplets from flowing into the diffusing hole 671 to obstruct diffusing.

Referring to FIGS. 2-4, in one embodiment of the present invention, the water baffle 63 comprises a plurality of retaining grooves 633 equiangularly spaced on the upper side thereof. The umbrella-shaped panel 67 has a plurality of engaging portions 675 located on the bottom surface thereof. By means of fastening the retaining grooves 633 to the respective engaging portions 675, the water baffle 350 is fastened to the umbrella-shaped panel 67. The joining method of fastening the retaining grooves 633 to the respective engaging portions 675 can be achieved by, for example a tight fit or hooking.

Referring to FIGS. 1-5, in one embodiment of the present invention, the hand wash cleaning and environmental purification diffuser further comprises a switch device 50. The switch device 50 comprises a power switch button, and the switch device 50 is electrically connected to the control unit 70. The bottom shell 10 is provided with a side hole 15. The switch device 50 is mounted in the side hole 15.

In some embodiments, the diffuser further comprises a light source device 51, which comprises, for example, an LED lamp or bulb, and a circuit device. The light source device 51 is mounted in the bottom shell 10 and electrically connected to the control unit 70. The umbrella-shaped panel 67, the tank cover 35, the shield 355, the water tank 30 and the water baffle 63 can be made of translucent or transparent plastic, acrylic, ceramic or glass, etc. The control unit 70 is electrically connected to an external power source to provide electrical power to the light source device 51, so that the light source device 51 emits light through the translucent or transparent water tank 30 and the tank cover 35 onto the umbrella-shaped panel 67 to provide a light decoration effect. The light falling upon the light-permeable translucent or transparent umbrella-shaped panel 67 is refracted by the radial ribs 673 to produce a light decoration effect that shows the skeleton charm of a paper umbrella. Combining the mist diffusing effect of the hand wash cleaning and environmental purification diffuser, the diffuser can have a better atmosphere in a gaseous environment. In particular, the water tank 30 can also be additionally added with a fragrance liquid to make the sterilization, disinfection and deodorization smell better.

In some embodiments, the control unit 70 comprises any of various printed circuit board assemblies such as electronic circuits or various computer equipment such as computers or microprocessors, which can be used in the operation or control function of the hand wash cleaning and environmental purification diffuser of the present invention.

In one embodiment of the hand wash cleaning and environmental purification diffuser of the present invention, the user fills a cleaning, sterilizing, disinfecting and/or deodorizing liquid into the water tank 30.

For example, select alkaline ionized water with a pH value of 10.0 or more, such as electrolysis of alkaline ionized water with a pH value of 10.5, 11, 11.5, 12, and 12.5. In the preferred embodiment, for example, the pH value of the hydroxide ionized water of pure water electrolysis is 10 to 12.5, and the alkaline ionized water has a peeling effect, can neutralize static electricity, and float away from dirt; alkalization can decompose oil or protein and has stronger permeability than general water, with good cleaning and sterilization effects.

In one embodiment, the electrolyzed hydroxide ion water with a pH value of 12.5 is filled into the oscillation space 32 of the water tank 30. The user turns on the power of the switch device 50 to the control unit 70 to instruct the first fan 20 and the first oscillation device 40 to operate, and the first oscillation device 40 generates vibration, causing the alkaline ionized water in the oscillation space 32 to generate mist. At the same time, the first fan 20 sucks in the outside air through the first air inlet 12 of the bottom shell 10. The suction air passes through the air flow channel 37 to the shield 355 and flows into the oscillation space 32. The generated mist of alkaline ionized water is carried by the air flow to pass from the oscillation space 32 through the first exhaust hole 357 and the diffusing hole 671 to the environment space outside the hand wash cleaning and environmental purification diffuser to sterilize, clean, deodorize, eliminate viruses or purify the air. The hand wash cleaning and environmental purification diffuser is safe to use and does not affect human health. When a person places the hands above the diffusing cover 60 of the hand wash cleaning and environmental purification diffuser of the present invention, the sensor 90 detects the presence of the hands and transmits the detected signal to the control unit 70. Upon receipt of the signal from the sensor 90, the control unit 70 drives the second oscillation device 45 to operate, so that the second oscillation device 45 is used in conjunction with the first oscillation device 40 to oscillate and atomize the liquid in the oscillation space 32 to produce a large number of atomized alkaline ionized water mist gas water molecules to clean, sterilize and disinfect the hands. When the user's hands leave above the diffusing cover 60, and the sensor 90 does not detect the hands, and the sensor 90 transmits a signal to the control unit 70 to instruct the second oscillation device 45 to turn off.

Referring to FIGS. 2-4, in one embodiment of the present invention, the diffuser further comprises a second fan 22 mounted in the chamber 11 and electrically connected to the control unit 70. The second fan 22 can be switched on/off by the switch device 50. The control unit 70 can be configured to provide a temperature sensor to detect the temperature in the chamber 11. When the temperature in the chamber 11 reaches a predetermined temperature value, the switch device 50 or the control unit 70 drives the second fan 22 to operate and to cool down the first oscillator 43, the second oscillator 49 and the control unit 70. The air flow produced by the second fan 22 flows from the air inlet 12 into the vent 373 toward the protruding pipe vent 371. The increased air flow can flow to the oscillation space 32, which can assist the first fan 20 to add atomized water molecules to the oscillation space, and quickly and efficiently transport to the diffusing hole 671 with a more abundant air flow, and then escape to the external space of the diffuser or the user's hands.

Referring to FIGS. 2-4, in one embodiment of the present invention, the water tank 30 also comprises a water level measuring column 38 and a drain 39. The water level measuring column 38 protrudes upwardly from the bottom of the water tank to a predetermined height. The drain 39 is opened on one side of the slot 31 and provided with an erected water guiding wall 391 on each of two opposite sides thereof. The user opens the tank cover 35 from the slot 31 to fill the liquid. At this time, the height of the water level measuring column 38 can be used as the basis for measuring whether the liquid exceeds the appropriate capacity of the water tank 30. If the level of the liquid exceeds the water level measuring column 38, the user can tilt the water tank 30, and use the water guiding walls 391 to drain the liquid from the drain 39 to a predetermined location to avoid spilling elsewhere.

Referring to FIGS. 2 and 3, in one embodiment of the present invention, the diffusing cover 60 further comprises a decorative cover 677. The decorative cover 677 has a plurality of overlapping diffusing holes 671'. The decorative cover 677 is combined with the umbrella-shaped panel 67 to form a decorative effect. These overlapping diffusing holes 671' correspond to the diffusing holes 671 for allowing the mist produced to pass therethrough to the external space.

Although particular embodiments of the present invention have been described in detail for purposes of illustration, various modifications and enhancements may be made without departing from the spirit and scope of the invention. Accordingly, the invention is not to be limited except as by the appended claims.

What the invention claimed is:

1. A hand wash cleaning and environmental purification diffuser, comprising a bottom shell, a first fan, a water tank, a first oscillation device, a diffusing cover and a control unit, wherein:
    said bottom shell comprises a chamber internally defined, a first air inlet provided on a bottom side of said chamber, and an opening formed on an upper edge of said chamber;
    said water tank is combined in said chamber, comprising a slot, an oscillation space, a tank bottom, a first hole, a tank cover and an air flow channel, said slot being formed on an upper side of said water tank, the interior of said water tank defining said oscillation space containing a liquid, said tank bottom opening said first hole, said air flow channel having one side thereof protruding in said oscillation space of said water tank to form a protruding pipe vent and an opposite side thereof extending out of said tank bottom to form a vent, said air flow channel being disposed in communication with said first air inlet through said chamber;
    said first fan is combined in said vent and disposed in communication with said first air inlet through said chamber;
    said tank cover comprises a shield and a first exhaust hole, said shield forming a recess shape on an inner side circumference of said tank cover, said first exhaust hole being formed on an opposite side of said tank cover, said tank cover being detachably covered on said slot, said shield covering outside of said protruding pipe vent, said protruding pipe vent and said first exhaust hole being disposed in communication with said oscillation space;
    said first oscillation device is mounted in said first hole and comprises a first oscillator, said first oscillator being externally coated with a layer of acid and alkali resistant coating;
    said diffusing cover comprises a diffusing hole, said diffusing cover being detachably assembled in said opening of said bottom shell to shield said tank cover, said diffusing hole communicating with said first exhaust hole and said oscillation space;
    said control unit is combined in said chamber at one side of said tank bottom and electrically connected with said first oscillation device and said first fan.

2. The hand wash cleaning and environmental purification diffuser as claimed in claim 1, further comprising a second oscillation device and a sensor said control unit is electrically connected with said second oscillation device, wherein:
    said water tank further comprises a second hole formed on said tank bottom;
    said second oscillation device is combined in said second hole;
    said sensor is combined in said chamber at one side of said tank bottom and electrically connected to said control unit;
    said second oscillation device comprises a second oscillator, said second oscillator being externally coated with a layer of acid and alkali resistant coating.

3. The hand wash cleaning and environmental purification diffuser as claimed in claim 2, wherein said acid and alkali resistant coating comprises a fluorine-containing polymer (fluoropolymer) or fluorine-containing oligomers or electronic metal coating agent.

4. The hand wash cleaning and environmental purification diffuser as claimed in claim 2, wherein the film thickness of the acid and alkali resistant coating is 0.5 to 1.5 microns.

5. The hand wash cleaning and environmental purification diffuser as claimed in claim 4, wherein the film thickness of the acid and alkali resistant coating is 1 micron.

6. The hand wash cleaning and environmental purification diffuser as claimed in claim 1, wherein said shield covers the outside of said protruding pipe vent of said air flow channel, and said protruding pipe vent forms a height relative to an inner wall of said tank cover.

7. The hand wash cleaning and environmental purification diffuser as claimed in claim 6, wherein an opening direction of said protruding pipe vent is perpendicular to an inner side wall of said tank cover and at the same time facing the inner wall of said tank cover.

8. The hand wash cleaning and environmental purification diffuser as claimed in any of claim 7, wherein said diffusing cover further comprises an umbrella-shaped panel, said umbrella-shaped panel being opened with said diffusing hole.

9. The hand wash cleaning and environmental purification diffuser as claimed in claim 8, further comprising a light source device mounted in said bottom shell and electrically connected to said control unit, wherein said umbrella-shaped panel, said tank cover, said shield, said water tank and said water baffle are selectively made of a light-permeable translucent or transparent material.

10. The hand wash cleaning and environmental purification diffuser as claimed in any of claim 1, wherein said diffusing cover further comprises an umbrella-shaped panel, said umbrella-shaped panel being opened with said diffusing hole.

11. The hand wash cleaning and environmental purification diffuser as claimed in any of claim 2, wherein said diffusing cover further comprises an umbrella-shaped panel, said umbrella-shaped panel being opened with said diffusing hole.

12. The hand wash cleaning and environmental purification diffuser as claimed in claim 11, wherein said diffusing cover further comprises a water baffle combined with a lower side of said umbrella-shaped panel, so that a gap is maintained between said water baffle and the lower side of said first exhaust hole.

13. The hand wash cleaning and environmental purification diffuser as claimed in claim 12, further comprising a light source device mounted in said bottom shell and electrically connected to said control unit, wherein said umbrella-shaped panel, said tank cover, said shield, said water tank and said water baffle are selectively made of a light-permeable translucent or transparent material.

14. The hand wash cleaning and environmental purification diffuser as claimed in claim 12, the water baffle comprises a plurality of retaining grooves equiangularly spaced on an upper side thereof, the umbrella-shaped panel has a plurality of engaging portions located on the bottom surface thereof, by means of fastening the retaining grooves to the respective engaging portions, the water baffle is fastened to the umbrella-shaped panel.

15. The hand wash cleaning and environmental purification diffuser as claimed in claim 1, wherein said water tank further comprises a water level measuring column and a drain, said water level measuring column protruding upwardly from bottom of said water tank to a predetermined height, said drain being opened on one side of said slot and provided with an erected water guiding wall on each of two opposite sides thereof.

16. The hand wash cleaning and environmental purification diffuser as claimed in claim 1, further comprising a second fan mounted in said chamber and electrically connected to said control unit.

17. The hand wash cleaning and environmental purification diffuser as claimed in claim 1, the diffusing cover further comprises a decorative cover, the decorative cover has a plurality of overlapping diffusing holes, the decorative cover is combined with the umbrella-shaped panel, these overlapping diffusing holes correspond to the diffusing holes.

* * * * *